US010757854B2

(12) United States Patent
Stanhope (10) Patent No.: US 10,757,854 B2
(45) Date of Patent: Sep. 1, 2020

(54) DETERMINING FORCES EXERTED ON ROLLING AGRICULTURAL COMPONENTS BASED ON AN APPLIED BRAKING FORCE

(71) Applicant: CNH Industrial America LLC, New Holland, PA (US)

(72) Inventor: Trevor P. Stanhope, Darien, IL (US)

(73) Assignee: CNH Industrial America LLC, New Holland, PA (US)

( * ) Notice: Subject to any disclaimer, the term of this patent is extended or adjusted under 35 U.S.C. 154(b) by 183 days.

(21) Appl. No.: 16/113,108

(22) Filed: Aug. 27, 2018

(65) Prior Publication Data
US 2020/0060068 A1 Feb. 27, 2020

(51) Int. Cl.
| A01B 76/00 | (2006.01) |
| G01N 33/24 | (2006.01) |
| G01L 5/00 | (2006.01) |
| A01B 49/02 | (2006.01) |
| A01B 49/06 | (2006.01) |
| A01B 63/32 | (2006.01) |

(52) U.S. Cl.
CPC ............ *A01B 76/00* (2013.01); *G01L 5/0052* (2013.01); *G01N 33/246* (2013.01); *A01B 49/027* (2013.01); *A01B 49/06* (2013.01); *A01B 63/32* (2013.01); *G01N 2033/245* (2013.01)

(58) Field of Classification Search
CPC ...... A01B 49/027; A01B 76/00; G01L 5/0052
USPC ............................................. 172/2, 518, 528
See application file for complete search history.

(56) References Cited

U.S. PATENT DOCUMENTS

| 3,834,481 A | 9/1974 | Carlson |
| 6,937,939 B1 | 8/2005 | Shibusawa et al. |
| 7,756,671 B2 | 7/2010 | Bertrand |
| 8,001,848 B2 | 8/2011 | White et al. |
| 8,738,244 B2 | 5/2014 | Lenz et al. |
| 8,827,001 B2 | 9/2014 | Wendte et al. |
| 9,167,742 B2 * | 10/2015 | Masten ............... A01B 79/005 |

(Continued)

FOREIGN PATENT DOCUMENTS

WO WO2012/107006 A1 8/2012

OTHER PUBLICATIONS

Tzach, Soil Sensors: A New Direction in Precision Agriculture to Improve Crop Production, Precision Ag, Apr. 10, 2018, 3 pages. http://www.precisionag.com/systems-management/soil-sensors-a-new-direction-in-precision-agriculture-to-improve-crop-production/.

*Primary Examiner* — Gary S Hartmann
(74) *Attorney, Agent, or Firm* — Rebecca L. Henkel; Rickard K. DeMille (57) ABSTRACT

In one aspect, a system for determining forces exerted on rolling ground engaging components of an agricultural implement may a ground engaging component configured to roll relative to soil within a field as the agricultural implement is moved across the field. A controller of the disclosed system may be configured to control an operation of a braking device such that a braking force is applied to the rolling ground engaging component. When the braking force is being applied to the rolling ground engaging component, the controller may be configured to monitor a rotational speed of the rolling ground engaging component based on measurement signals received from a sensor. Moreover, the controller may be configured to determine a force exerted on the rolling ground engaging component by the soil within (Continued)

the field based on the applied braking force and the monitored rotational speed.

20 Claims, 6 Drawing Sheets

(56) References Cited

U.S. PATENT DOCUMENTS

| | | |
|---|---|---|
| 9,334,827 B2 | 5/2016 | Seelke et al. |
| 9,826,677 B2 | 11/2017 | Gervais et al. |
| 9,904,963 B2 | 2/2018 | Rupp et al. |
| 9,943,027 B2 | 4/2018 | Sauder et al. |
| 2016/0223511 A1 | 8/2016 | Koshnick et al. |
| 2017/0090068 A1 | 3/2017 | Xiang et al. |
| 2018/0024271 A1 | 1/2018 | Koch et al. |
| 2020/0053948 A1* | 2/2020 | Zemenchik .......... H02K 49/065 |

* cited by examiner

DETERMINING FORCES EXERTED ON ROLLING AGRICULTURAL COMPONENTS BASED ON AN APPLIED BRAKING FORCE

FIELD OF THE INVENTION

The present disclosure generally relates to agricultural implements and, more particularly, to systems and methods for determining forces exerted on rolling ground engaging components of an agricultural implement based on an applied braking force.

BACKGROUND OF THE INVENTION

Modern farming practices strive to increase yields of agricultural fields. In this respect, agricultural implements are towed behind a tractor or other work vehicle to disperse seeds and other agricultural products throughout a field and/or condition the soil. An agricultural implement typically includes one or more rolling ground engaging components that are configured to roll relative to the soil as the implement is moved across a field. For example, in certain configurations, the implement may include one or more disc openers that form a furrow or trench within the soil while rolling relative to the soil. Furthermore, the implement may also include one or more closing discs that close the furrow while rolling relative to the soil. As the implement is moved across the field, the soil exerts a force or a rolling resistance on the rolling ground engaging components. Such force may be indicative of one or more characteristics of the soil within the field across which the implement is being moved.

Accordingly, an improved system and method for determining forces exerted on rolling ground engaging components of an agricultural implement would be welcomed in the technology.

SUMMARY OF THE INVENTION

Aspects and advantages of the technology will be set forth in part in the following description, or may be obvious from the description, or may be learned through practice of the technology.

In one aspect, the present subject matter is directed to a system for determining forces exerted on rolling ground engaging components of an agricultural implement. The system may include a rolling ground engaging component configured to roll relative to soil within a field as the agricultural implement is moved across the field. The system may also include a braking device configured to apply a braking force to the rolling ground engaging component. Furthermore, the system may include a sensor configured to detect a parameter indicative of a rotational speed of the rolling ground engaging component. Additionally, the system may include a controller communicatively coupled to the sensor. The controller may be configured to control an operation of the braking device such that a braking force is applied to the rolling ground engaging component. When the braking force is being applied to the rolling ground engaging component, the controller may be configured to monitor the rotational speed of the rolling ground engaging component based on measurement signals received from the sensor. Moreover, the controller may be configured to determine a force exerted on the rolling ground engaging component by the soil within the field based on the applied braking force and the monitored rotational speed.

In another aspect, the present subject matter is directed to a system for determining forces exerted on rolling ground engaging components of an agricultural implement. The system may include a rolling ground engaging component configured to roll relative to soil within a field as the agricultural implement is moved across the field. The system may also include a braking device configured to apply a braking force to the rolling ground engaging component. Furthermore, the system may include a sensor configured to detect a parameter indicative of a rotational speed of the rolling ground engaging component. Additionally, the system may include a controller communicatively coupled to the sensor. The controller may be configured to control an operation of the braking device in a manner that adjusts the braking force being applied to the rolling ground engaging component. When the braking force is being adjusted, the controller may be configured to monitor the rotational speed of the rolling ground engaging component based on measurement signals received from the sensor. Moreover, the controller may be configured to determine a force exerted on the rolling ground engaging component by the soil within the field based on a magnitude of an adjustment of the braking force and the monitored rotational speed.

In a further aspect, the present subject matter is directed to a method for determining forces exerted on rolling ground engaging components of an agricultural implement. The seed-planting implement may include a rolling ground engaging component configured to roll relative to soil within a field as the agricultural implement is moved across the field. The method may include controlling, with the computing device, an operation of a braking device such that a braking force is applied to the rolling ground engaging component. When the braking force is being applied to the rolling ground engaging component, the method may include monitoring, with the computing device, a rotational speed of the rolling ground engaging component. Furthermore, the method may include determining, with the computing device, a force exerted on the rolling ground engaging component based on the applied braking force and the monitored rotational speed.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Repeat use of reference characters in the present specification and drawings is intended to represent the same or analogous features or elements of the present technology.

DETAILED DESCRIPTION OF THE DRAWINGS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for determining forces exerted on rolling ground engaging components of an agricultural implement, such as a seed-planting implement. Specifically, in several embodiments, as the implement is being moved across a field, a controller of the disclosed system may be configured to control the operation of a braking device of the implement such that a braking force is applied or adjusted to a rolling ground engaging component(s) of the implement, such as one or more gauge wheels, disc openers, closing discs, press wheels, or residue removal wheels. The braking force(s) may, in turn, cause the rotational speed(s) of the rolling ground engaging component(s) to change, with the change(s) in rotational speed generally being indicative of the force(s) being applied to the rolling ground engaging component(s) by the soil within the field. As such, the controller may be configured to monitor the rotational speed(s) of the rolling ground engaging component(s) as the braking force(s) is being applied to or adjusted on the rolling ground engaging component(s). The controller may then be configured to determine the force(s) exerted on the rolling ground engaging component(s) by the soil based on the applied braking force(s) and the monitored rotational speed(s). Thereafter, the controller may be configured to determine a soil characteristic(s), such as soil density, soil plasticity, soil moisture, soil texture, and/or soil cohesion, of the soil within the field based on the determined force(s). Furthermore, in one embodiment, the controller may also be configured to adjust one or more operating parameters of the implement or an associated work vehicle, such as the downforce being applied to the rolling ground engaging component(s) and/or the ground speed of the work vehicle, based on the determined force(s).

Figure 1:
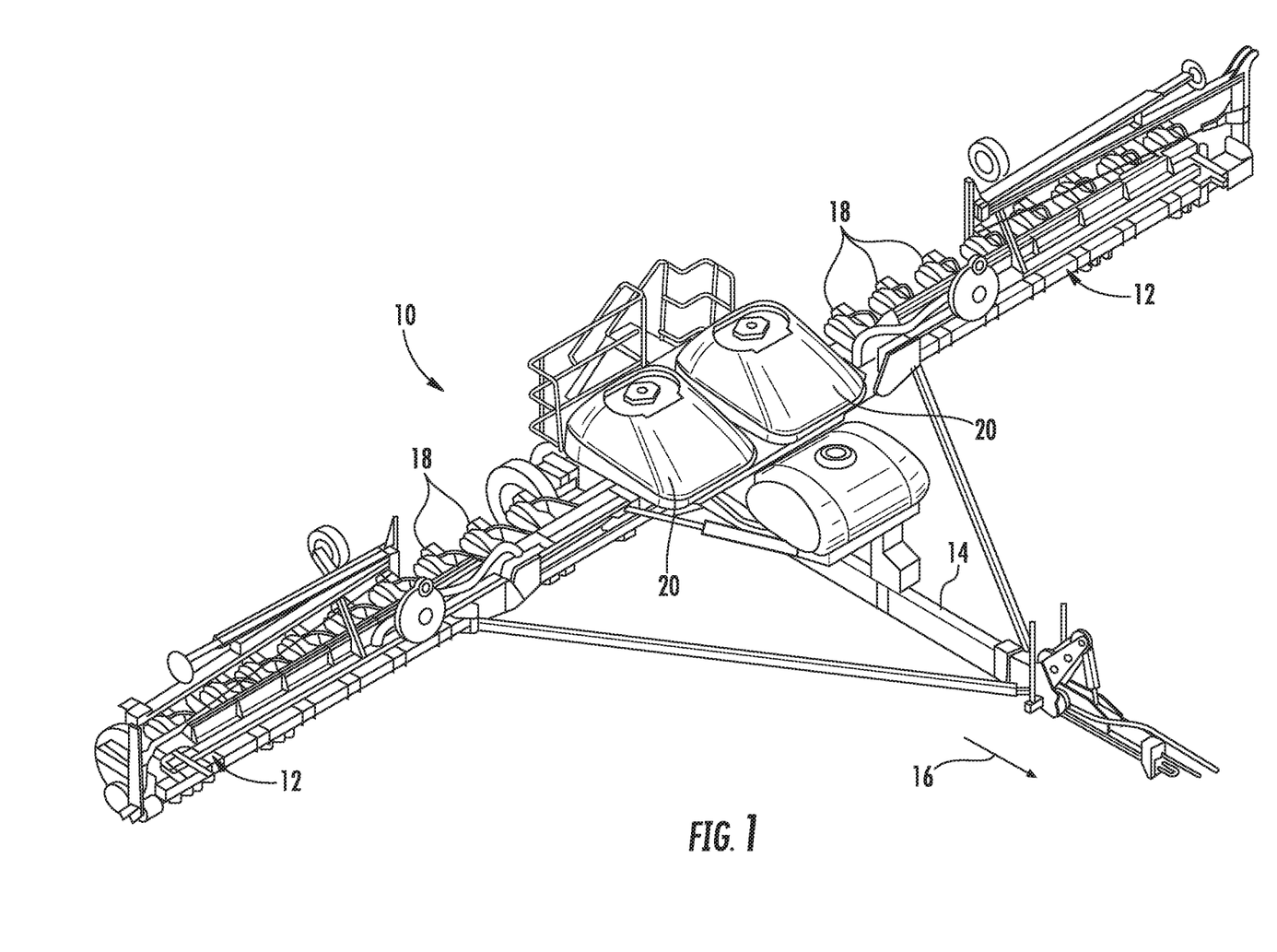
FIG. 1 illustrates a perspective view of one embodiment of an agricultural implement in accordance with aspects of the present subject matter.

Referring now to the drawings, FIG. 1 illustrates a perspective view of one embodiment of an agricultural implement 10 in accordance with aspects of the present subject matter. It should be appreciated that, although the implement 10 illustrated herein corresponds to a planter, the implement 10 may generally correspond to any suitable equipment or implement, such as a seeder (e.g., a seed disc drill) or another seed-planting implement, a side dresser or another fertilizer dispensing implement, a strip tiller, a disc harrow or other tillage implement, and/or the like.

As shown in FIG. 1, the implement 10 may include a laterally extending toolbar or frame assembly 12 connected at its middle to a forwardly extending tow bar 14 to allow the implement 10 to be towed by a work vehicle (not shown), such as an agricultural tractor, in a direction of travel (e.g., as indicated by arrow 16 in FIG. 1). The toolbar 12 may generally be configured to support a plurality of seed planting units (or row units) 18. As is generally understood, each row unit 18 may be configured to deposit seeds at a desired depth beneath the soil surface and at a desired seed spacing as the implement 10 is being towed by the work vehicle, thereby establishing rows of planted seeds. In some embodiments, the bulk of the seeds to be planted may be stored in one or more hoppers or seed tanks 20. Thus, as seeds are planted by the row units 18, a pneumatic distribution system may distribute additional seeds from the seed tanks 20 to the individual row units 18. Additionally, one or more fluid tanks 22 may store agricultural fluids, such as insecticides, herbicides, fungicides, fertilizers, and/or the like.

It should be appreciated that, for purposes of illustration, only a portion of the row units 18 of the implement 10 have been shown in FIG. 1. In general, the implement 10 may include any number of row units 18, such as six, eight, twelve, sixteen, twenty-four, thirty-two, or thirty-six row units. In addition, it should be appreciated that the lateral spacing between row units 18 may be selected based on the type of crop being planted. For example, the row units 18 may be spaced approximately thirty inches from one another for planting corn, and approximately fifteen inches from one another for planting soybeans.

It should also be appreciated that the configuration of the agricultural implement 10 described above and shown in FIG. 1 is provided only to place the present subject matter in an exemplary field of use. Thus, it should be appreciated that the present subject matter may be readily adaptable to any manner of implement configuration.

Figure 2:
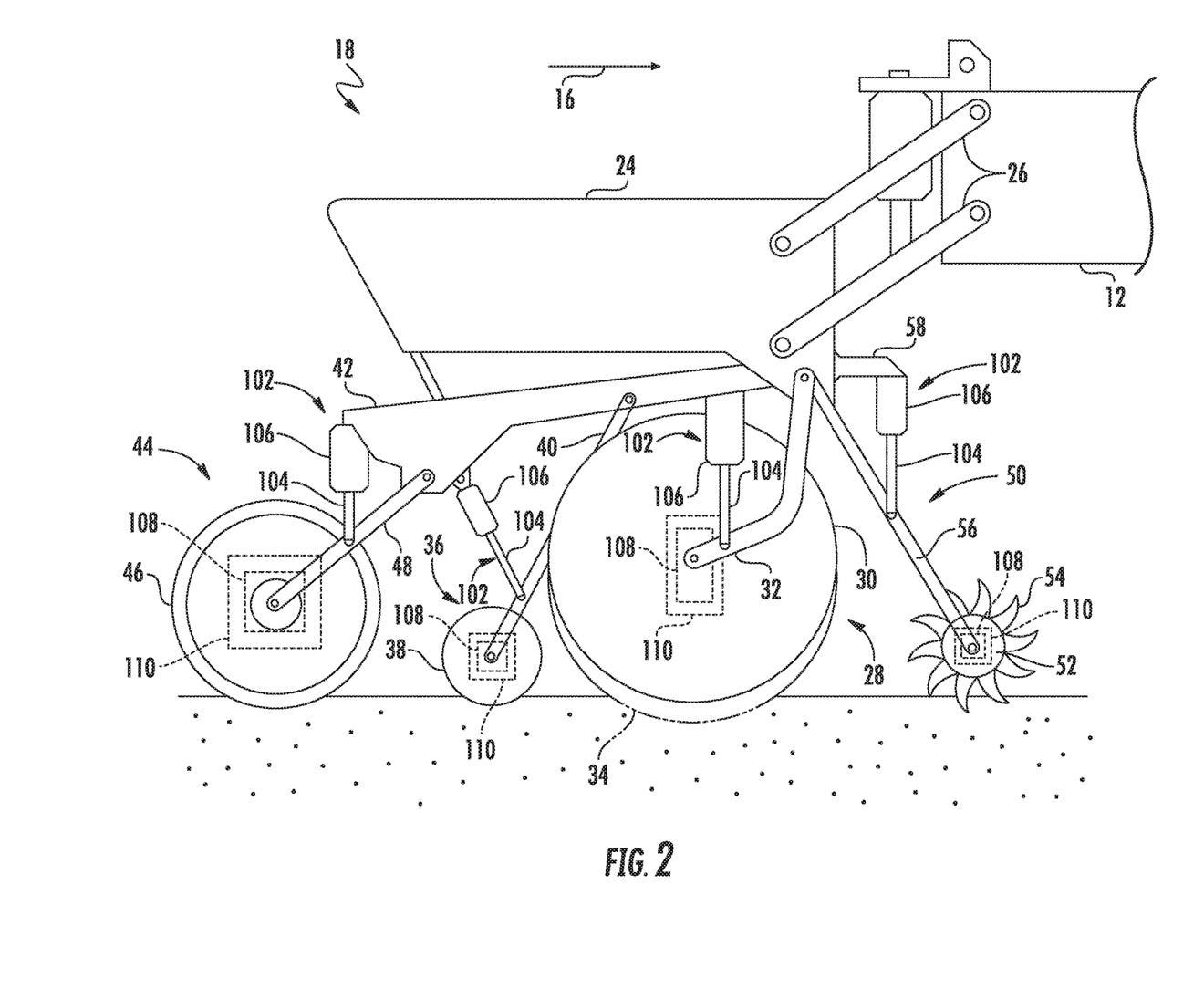
FIG. 2 illustrates a side view of one embodiment of a row unit suitable for use with an agricultural implement in accordance with aspects of the present subject matter.

Referring now to FIG. 2, a side view of one embodiment of a row unit 18 is illustrated in accordance with aspects of the present subject matter. As shown, the row unit 18 may include a frame 24 adjustably coupled to the toolbar 12 by links 26. For example, one end of each link 26 may be pivotably coupled to the frame 24, while an opposed end of each link 26 may be pivotably coupled to the toolbar 12. In one embodiment, the links 26 may be parallel. However, it should be appreciated that, in alternative embodiments, the row unit 18 may be coupled to the toolbar 12 in any other suitable manner. For example, the links 26 may be fixedly coupled to the frame 24 and/or the links 26 may be non-parallel. Additionally, in a further embodiment, the implement 10 may not include the links 26. In such instance, the implement 10 may include other components for coupling each row unit 18 to the toolbar 12.

As shown in FIG. 2, the row unit 18 also includes a furrow opening assembly 28. For example, in one embodiment, the furrow opening assembly 28 may include a gauge wheel 30 and one or more disc openers 34 configured to excavate a furrow or trench in the soil. As is generally understood, the gauge wheel 30 may be configured to engage the top surface of the soil as the implement 10 is moved across the field. In this regard, the height of the disc opener(s) 34 may adjusted with respect to the position of the gauge wheel 30 to set the desired depth of the furrow being excavated. Furthermore, the furrow opening assembly 28 may include a support arm 32 configured to adjustably couple the gauge wheel 30 and the disc opener(s) 34 to the frame assembly 24. For example, one end of the support arm 32 may be pivotably coupled to the gauge wheel 30 and the disc opener(s) 34, while an opposed end of the support arm 32 may be pivotably coupled to the frame 24. However, it should be appreciated that, in alternative embodiments, the gauge wheel 30 and the disc opener(s) 34 may be coupled to the frame 24 in any other suitable manner.

Moreover, as shown, the row unit 18 may include a furrow closing assembly 36. Specifically, in several embodiments, the furrow closing assembly 28 may include a pair of closing discs 38 (only of which is shown) positioned relative to each other in a manner that permits soil to flow between the discs 38 as the implement 10 is being moved across the field. As such, the closing discs 38 may be configured to close the furrow after seeds have been deposited therein, such as by pushing the excavated soil into the furrow. Furthermore, the furrow closing assembly 36 may include a support arm 40 configured to adjustably couple the closing discs 38 to the frame assembly 24. For example, one end of the support arm 40 may be pivotably coupled to the closing discs 38, while an opposed end of the support arm 40 may be pivotably coupled to a chassis arm 42, which is, in turn, coupled to the frame 24. However, it should be appreciated that, in alternative embodiments, the closing discs 38 may be coupled to the frame 24 in any other suitable manner. Furthermore, it should be appreciated that, in alternative embodiments, the furrow closing assembly 36 may include any other suitable number of closing discs 38, such as one closing disc 38 or three or more closing discs 38.

Additionally, the row unit 18 may include a press wheel assembly 44. Specifically, in several embodiments, the press wheel assembly 44 may include a press wheel 46 configured to roll over the closed furrow to firm the soil over the seed and promote favorable seed-to-soil contact. Furthermore, the press wheel assembly 44 may include a support arm 48 configured to adjustably couple the press wheel 46 to the frame assembly 24. For example, one end of the support arm 48 may be pivotably coupled to the press wheel 48, while an opposed end of the support arm 48 may be pivotably coupled to the chassis arm 42, which is, in turn, coupled to the frame 24. However, it should be appreciated that, in alternative embodiments, the press wheel 46 may be coupled to the frame 24 in any other suitable manner.

Furthermore, in one embodiment, a residue removal device 50 may be positioned at the forward end of the row unit 18 relative to the direction of travel 16. In this regard, the residue removal device 50 may be configured to break up and/or sweep away residue, dirt clods, and/or the like from the path of the row unit 18 before the furrow is formed in the soil. For example, in one embodiment, the residue removal device 50 may include one or more residue removal wheels 52, with each wheel 52 having a plurality of tillage points or fingers 54. As such, the wheel(s) 52 may be configured to roll relative to the soil as the implement 10 is moved across the field such that the fingers 54 break up and/or sweep away residue and dirt clods. Additionally, the residue removal device 50 may include a support arm 56 configured to adjustably couple the residue removal wheel(s) 52 to the frame assembly 24. For example, one end of the support arm 56 may be pivotably coupled to the wheel(s) 52, while an opposed end of the support arm 56 may be pivotably coupled to the frame 24. However, it should be appreciated that, in alternative embodiments, the residue removal wheel(s) 52 may be coupled to the frame 24 in any other suitable manner. Furthermore, although only one residue removal wheel 52 is shown in FIG. 2, it should be appreciated that, in alternative embodiments, the residue removal device 50 may include any other suitable number of residue removal wheels 52. For example, in one embodiment, the residue removal device 50 may include a pair of residue removal wheels 52.

In several embodiments, the row unit 18 may include one or more actuators 102. Specifically, each actuator 102 may be configured to adjust to the position of a rolling ground engaging component of the row unit 18 relative to the frame 24. As used herein, a rolling ground engaging component may be any component of the implement 10 configured to roll relative to the soil as the implement 10 is moved across a field. For example, in one embodiment, a first end of each actuator 102 (e.g., a rod 104 of each actuator 102) may be coupled to an arm on which the rolling ground engaging component is mounted, while a second end of each actuator 102 (e.g., the cylinder 106 of each actuator 102) may be coupled to the chassis arm 42 or a bracket 58, which are, in turn, coupled to the frame 24. The rod 104 of each actuator 102 may be configured to extend and/or retract relative to the corresponding cylinder 106 to adjust the downforce being applied to and/or the penetration depth of the associated rolling ground engaging component. In one embodiment, the actuator(s) 102 corresponds to a fluid-driven actuator(s), such as a hydraulic or pneumatic cylinder(s). However, it should be appreciated that the actuator(s) 102 may correspond to any other suitable type of actuator(s), such as an electric linear actuator(s). Furthermore, it should be appreciated that, in alternative embodiments, the actuator(s) 102 may be configured to adjust to the position(s) of any other rolling ground engaging component(s) of the row unit 18, such as the disc opener(s) 34.

As shown in FIG. 2, the actuator(s) 102 may be configured to adjust the downforce being applied to and/or the penetration depth of any number of rolling ground engaging components of the row unit 18. Specifically, in several embodiments, the actuator(s) 102 may configured to adjust the downforce being applied to one or more rolling ground engaging components of the furrow opening assembly 28, the furrow closing assembly 36, the press wheel assembly 44, and/or the residue removal device 50. For instance, as shown in the illustrated embodiment, an actuator 102 may configured to adjust the downforce being applied to the gauge wheel 30, the closing disc(s) 38, the press wheel 46, and the residue removal wheel(s) 52. Furthermore, in the illustrated embodiment, the actuators 102 may be configured to adjust the penetration depth of the closing disc(s) 38. Alternatively, the actuator(s) 102 may be provided in operative association with any other suitable rolling ground engaging components of the row unit 18, such as the disc opener(s) 34.

Moreover, in several embodiments, the row unit 18 may include one or more rotational speed sensors 108. Specifically, each rotational speed sensor 108 may be configured to detect a parameter associated with the rotational speed of an associated rolling ground engaging component of the row unit 18. For example, in one embodiment, each rotational speed sensor 108 may be configured as a Hall Effect sensor configured to detect the rotational speed of the associated rolling ground engaging component. However, it should be appreciated that, in alternative embodiments, the rotational speed sensor(s) 108 may be configured as any other suitable device(s) for sensing or detecting the rotational speed(s) or position(s) of the one or more rolling ground engaging component(s) of the row unit 18.

Furthermore, as shown in FIG. 2, the rotational speed sensor(s) 108 may be provided in operative association with any number of rolling ground engaging components of the row unit 18. Specifically, in several embodiments, the rotational speed sensor(s) 108 may be provided in operative association with one or more rolling ground engaging components of the furrow opening assembly 28, the furrow closing assembly 36, the press wheel assembly 44, and/or the residue removal device 50. For instance, as shown in the illustrated embodiment, a rotational speed sensor 108 may be provided in operative association with the gauge wheel 30, one of the closing discs 38, the press wheel 46, and one of the residue removal wheels 52. Alternatively, the rotational speed sensor(s) 108 may be provided in operative association with any other suitable rolling ground engaging components of the row unit 18, such as the disc opener(s) 34 and/or additional closing discs 38 or residue removal wheels 52.

In accordance with aspects of the present subject matter, the row unit 18 may include one or more braking devices 110. Specifically, each braking device 110, when activated, may be configured to apply a braking force to an associated rolling ground engaging component of the row unit 18. For example, in one embodiment, the braking device(s) 110 may correspond to a non-contact-based braking device(s), such as a hysteresis brake(s). In general, a hysteresis brake may include a rotor or drag cup positioned within a pole structure such that an air gap is defined between the rotor and the pole structure. As such, the rotor may be configured to rotate relative to the pole structure. When a field coil embedded within the rotor is magnetized (e.g., by applying an electric current thereto), a magnetic torque is generated within the air gap. The magnetic torque may, in turn, cause the rotor to rotate in a manner that creates a braking force. In another embodiment, the braking device(s) 110 may correspond to a suitable hydraulic cylinder(s) or an electric actuator(s) configured to push a stationary frictional element(s), such as a brake shoe(s) or a brake caliper(s), against a rotating element(s), such as a brake drum(s) or a brake disc(s). However, it should be appreciated that, in alternative embodiments, the braking device(s) 110 may be configured as any other suitable device(s) for applying a braking force(s) to one or more rolling ground engaging components of the row unit 18.

Additionally, as shown in FIG. 2, the braking device(s) 110 may be provided in operative association with any number of rolling ground engaging components of the row unit 18. Specifically, in several embodiments, the braking device(s) 110 may be provided in operative association with one or more rolling ground engaging components of the furrow opening assembly 28, the furrow closing assembly 36, the press wheel assembly 44, and/or the residue removal device 50. For instance, as shown in the illustrated embodiment, a braking device 110 may be provided in operative association with the gauge wheel 30, one of the closing discs 38, the press wheel 46, and one of the residue removal wheels 52. In one embodiment, the braking device(s) 110 may be provided in operative association with the rolling ground engaging component(s) of the row unit 18 to which a rotational speed sensor(s) 108 is operatively associated. Alternatively, the rotational speed sensor(s) 108 may be provided in operative association with any other suitable rolling ground engaging components of the row unit 18, such as the disc opener(s) 34 and/or additional closing discs 38 or residue removal wheels 52.

It should be appreciated that the configuration of the row unit 18 described above and shown in FIG. 2 is provided only to place the present subject matter in an exemplary field of use. Thus, it should be appreciated that the present subject matter may be readily adaptable to any manner of row unit configuration.

Figure 3:
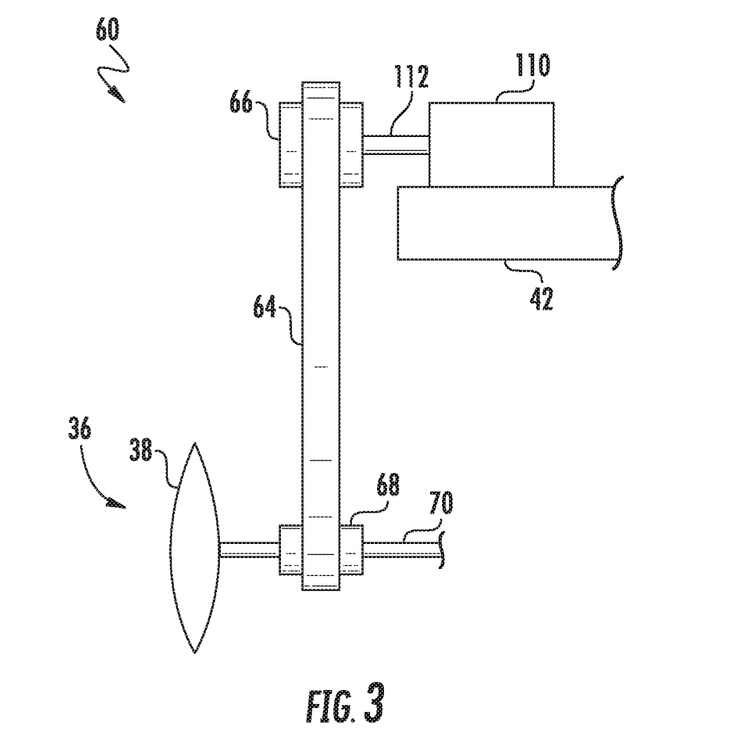
FIG. 3 illustrates a front view of one embodiment of a braking force transmission assembly in accordance with aspects of the present subject matter, particularly illustrating the assembly configured to transmit a braking force from a braking device to a closing disc of an agricultural implement.
Figure 4:
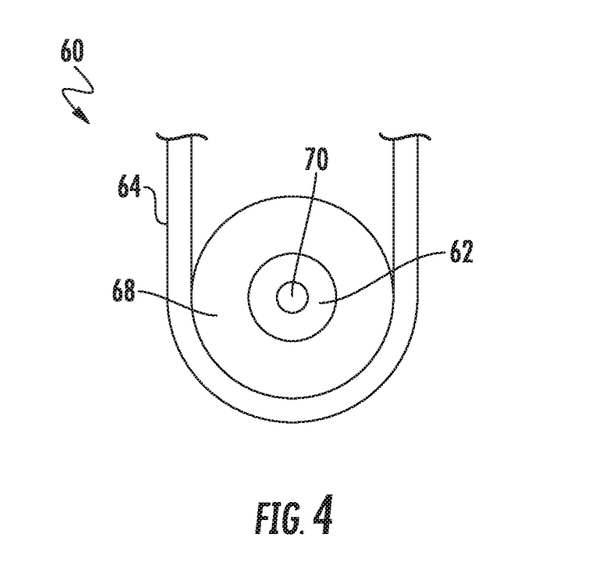
FIG. 4 illustrates a partial, side view of the braking force transmission assembly shown in FIG. 3, particularly illustrating a clutch of the system in accordance with aspects of the present subject matter.

Referring now to FIGS. 3 and 4, differing views of one embodiment of a braking force transmission assembly 60 of the row unit 18 are illustrated in accordance with aspects of the present subject matter. Specifically, FIG. 3 illustrates a front view of the transmission assembly 60, particularly illustrating various components thereof. Additionally, FIG. 4 illustrates a partial, side view of the transmission assembly 60, particularly illustrating a clutch 62 of the assembly 60. As shown in FIG. 3, the transmission assembly 60 may be configured to transmit a braking force from a braking device 110 of the row unit 18 to one of the closing discs 38 of the furrow closing assembly 36. However, it should be appreciated that any suitable transmission assembly may be utilized to transmit the braking force from the braking device 110 to the closing disc 38. Furthermore, it should be appreciated that the disclosed transmission assembly 60 may be configured to transmit a braking force from any braking device 110 of the row unit 18 to any rolling ground engaging component of the row unit 18, such as the gauge wheel 30, the disc opener(s) 34, the press wheel 46, and/or the residue removal wheel 52.

As shown in FIG. 3, the transmission assembly 60 may include a flexible, endless member 64 configured to transmit the braking force from the braking device 110 to the closing disc 38. More specifically, in the illustrated embodiment, the braking device 110 may be configured as a non-contact-based braking device mounted on the chassis arm 42 of the row unit 18 at a position located generally above the closing discs 38. In this regard, the member 64 may be configured to frictionally engage a pulley 66 coupled to an output shaft 112 of the braking device 110 and a pulley 68 coupled to an axle 70 on which the closing disc 38 is mounted. When the braking device 110 is activated, its output shaft 112 may rotate in the opposite direction of the rotation of the axle 70. As such, the member 64 may be configured to transmit the rotational energy from the output shaft 112 to the axle 70. Such rotational energy may be in the direction opposite of the rotation of the axle 70, thereby providing a braking force to the closing disc 38. It should be appreciated that the flexible, endless member 64 may be configured as a belt (e.g., V-belts), a chain, or any other suitable member for transmitting rotational energy between the braking device 110 and the closing disc 38. Furthermore, it should be appreciated that, in alternative embodiments, the braking device 110 may be directly coupled to or otherwise integrated into the axle 70 such that the magnetic torque generated by the braking device 110 is directly applied to the axle 70.

Referring now to FIG. 4, the transmission assembly 60 may include a clutch 62. For example, as shown, in one embodiment, the clutch 62 may be coupled between the axle 70 of the closing disc 38 and the associated pulley 68. As such, when the clutch 62 is disengaged, the clutch 62 may be configured to permit the closing discs 38 and the axle 70 to rotate without also rotating the flexible member 64 and the output shaft 112 of the braking device 110. Conversely, when the clutch 62 is engaged, the clutch 62 may be configured to mechanically couple the axle 70 and the associated pulley 68 in a manner that transmits the braking force from the braking device 110 to the closing disc 38. However, it should be appreciated that, in alternative embodiments, the clutch 68 may be coupled between the output shaft 112 and the associated pulley 66. In such embodiments, the clutch 62 may be configured to permit the closing disc 38, the axle 70, and the flexible member 64 to rotate without also rotating the corresponding output shaft 112 of the braking device 110.

Moreover, it should be appreciated that the clutch 62 may be configured as any suitable device that permits selective engagement and disengagement of the braking device 110 and the closing disc 38. For example, in one embodiment, the clutch 62 may include a suitable actuator (e.g., an electric linear actuator) configured to engage and disengage a pair of friction plates, with one friction plate being coupled to the braking device 110 and the other friction plate and coupled to the closing disc 38. Conversely, in another embodiment, the clutch 62 may be configured as a purely mechanical device, such as a Sprag clutch.

Additionally, it should be appreciated that the configuration of the brake force transmission assembly 60 described above and shown in FIGS. 3 and 4 is provided only to place the present subject matter in an exemplary field of use. Thus, it should be appreciated that the present subject matter may be readily adaptable to any manner of transmission assembly configuration.

Figure 5:
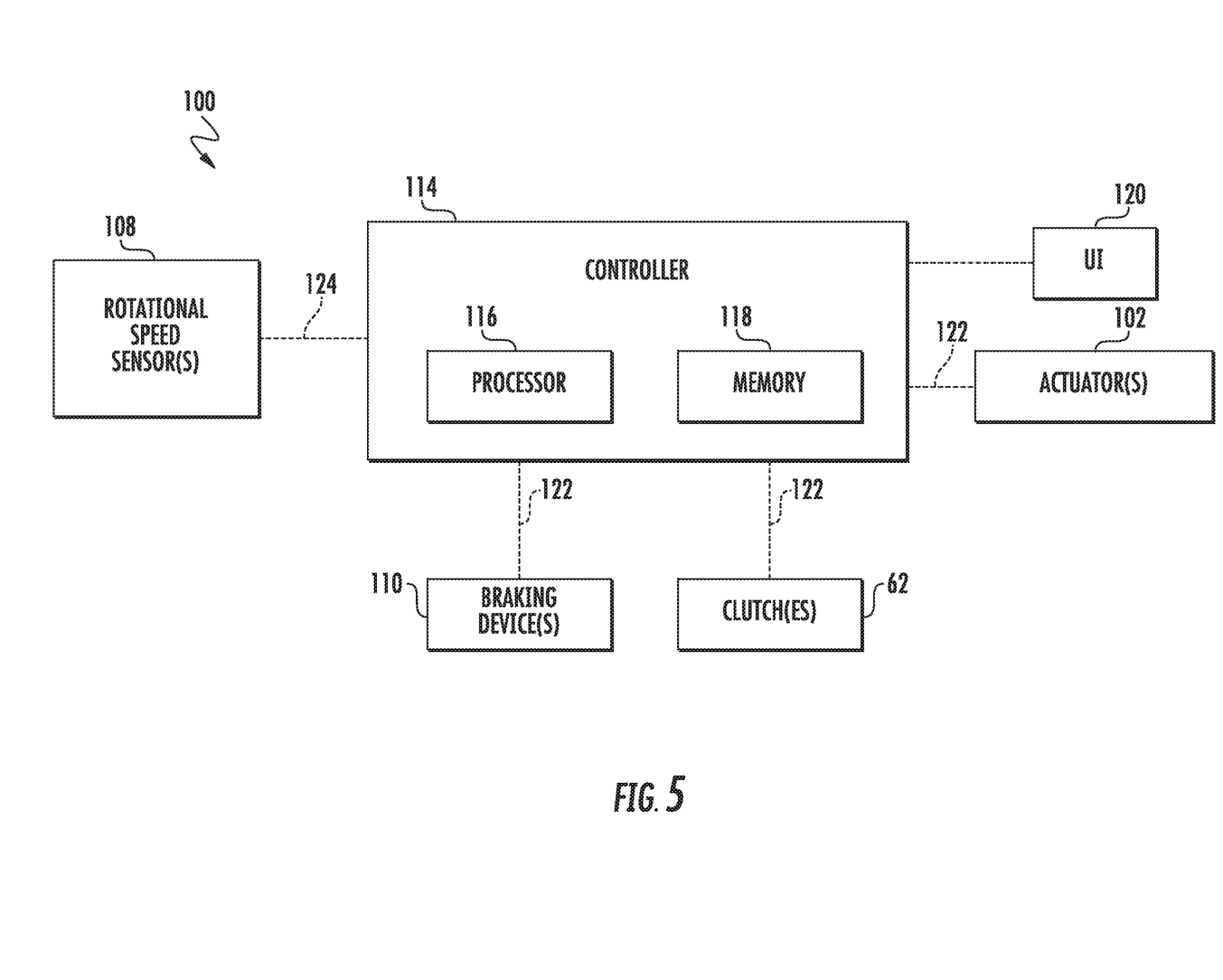
FIG. 5 illustrates a schematic view of one embodiment of a system for determining forces exerted on rolling ground engaging components of an agricultural implement in accordance with aspects of the present subject matter.

Referring now to FIG. 5, a schematic view of one embodiment of a system 100 for determining forces exerted on rolling ground engaging components of an agricultural implement is illustrated in accordance with aspects of the present subject matter. In general, the system 100 will be described herein with reference to the implement 10, the row unit 18, and the transmission assembly 60 described above with reference to FIGS. 1-4. However, it should be appreciated by those of ordinary skill in the art that the disclosed system 100 may generally be utilized with s agricultural implements having any other suitable implement configuration, row units having any other suitable row unit configuration, and/or transmission assemblies having any other suitable assembly configuration.

As shown in FIG. 5, the system 100 may include a controller 114 configured to electronically control the operation of one or more components of the implement 10. In general, the controller 114 may comprise any suitable processor-based device known in the art, such as a computing device or any suitable combination of computing devices. Thus, in several embodiments, the controller 114 may include one or more processor(s) 116 and associated memory device(s) 118 configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 118 of the controller 114 may generally comprise memory element(s) including, but not limited to, a computer readable medium (e.g., random access memory (RAM)), a computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 118 may generally be configured to store suitable computer-readable instructions that, when implemented by the processor(s) 116, configure the controller 114 to perform various computer-implemented functions, such as one or more aspects of the methods 200 and 300 described below with reference to FIGS. 6 and 7. In addition, the controller 114 may also include various other suitable components, such as a communications circuit or module, one or more input/output channels, a data/control bus and/or the like.

It should be appreciated that the controller 114 may correspond to an existing controller of the implement 10 or an associated work vehicle (not shown) or the controller 114 may correspond to a separate processing device. For instance, in one embodiment, the controller 114 may form all or part of a separate plug-in module that may be installed within the implement 10 or associated work vehicle to allow for the disclosed system and method to be implemented without requiring additional software to be uploaded onto existing control devices of the implement 10 or the associated work vehicle.

Furthermore, in one embodiment, the system 100 may also include a user interface 120. More specifically, the user interface 120 may be configured to provide feedback (e.g., notifications associated with forces exerted on rolling ground engaging components of the implement 10) to the operator of the implement 10. As such, the user interface 120 may include one or more feedback devices (not shown), such as display screens, speakers, warning lights, and/or the like, which are configured to communicate such feedback. In addition, some embodiments of the user interface 120 may include one or more input devices (not shown), such as touchscreens, keypads, touchpads, knobs, buttons, sliders, switches, mice, microphones, and/or the like, which are configured to receive user inputs from the operator. In one embodiment, the user interface 120 may be positioned within a cab of a work vehicle configured to tow the implement 10 across the field. However, in alternative embodiments, the user interface 120 may have any suitable configuration and/or be positioned in any other suitable location.

In several embodiments, the controller 114 may be configured to control the operation of the braking device(s) 110 such that a braking force is applied to one or more rolling ground engaging components of the implement 10, such as the gauge wheel 30, the disc opener(s) 34, the closing disc(s) 38, the press wheel 46, and/or the residue removal wheel(s) 52. Specifically, as shown in FIG. 5, the controller 114 may be communicatively coupled to the braking device(s) 110 via a wired or wireless connection to allow control signals (e.g., as indicated by dashed lines 122 in FIG. 5) to be transmitted from the controller 114 to the braking device(s) 110. In this regard, the controller 114 may be configured to transmit control signals 122 to the braking device(s) 110 instructing the braking device(s) 110 to apply a braking force to the associated rolling ground engaging component(s). In general, the amount or magnitude of the applied braking force may be a known value. Alternatively, the controller 114 may be configured to transmit control signals 122 to the braking device(s) 110 instructing the braking device(s) 110 to adjusted (e.g., increase or decrease) the braking force being applied to the associated rolling ground engaging component(s). The amount or magnitude of the change in braking force may be a known value.

In one embodiment, the controller 114 may be configured to control the operation of the clutch(es) 62 when the braking force is applied to one or more rolling ground engaging components of the implement 10. As indicated above, the clutch(es) 62 may be configured to selectively transmit the braking force(s) from the associated braking device(s) 110 to the associated rolling ground engaging component(s). In this regard, as shown in FIG. 5, the controller 114 may be communicatively coupled to the clutch(es) 62 (e.g., an actuator(s) of the clutch(es) 62) via a wired or wireless connection to allow control signals 122 to be transmitted from the controller 114 to the clutch(es) 62. As such, when the braking device(s) 110 is activated, the controller 114 may be configured to transmit control signals 122 to the corresponding clutch(es) 62 instructing the clutch(es) 62 to engage in a manner that transmits the braking force(s) from the corresponding braking device(s) 110 to the corresponding rolling ground engaging component(s). Alternatively, the braking force(s) may be transmitted directly from the braking device(s) 110 to the associated rolling ground engaging component(s) without requiring control of any other component(s) of the system 100 coupled between the braking device(s) 110 and the associated rolling ground engaging component(s).

It should be appreciated that, in several embodiments, the duration over which the braking force(s) is applied to the rolling ground engaging component(s) may generally be sufficiently short to prevent such braking force(s) from impeding the operation of the rolling ground engaging component(s). For example, in one embodiment, the duration over which the braking force(s) is applied may be less than 1 second, such as less than 0.8 seconds, less than 0.6 seconds, less than 0.4 seconds, and/or less than 0.2 seconds. However, in alternative embodiments, the duration over which the braking force(s) is applied may be any other suitable time duration. Furthermore, in one embodiment, the braking force may be continuously applied during operation of the implement 10.

When the braking force(s) is being applied to or adjusted on the rolling ground engaging component(s), the controller 114 may be configured to monitor the rotational speed(s) of the rolling ground engaging component(s). Specifically, as shown in FIG. 5, the controller 114 may be communicatively coupled to rotational speed sensor(s) 108 via wired or wireless connection to allow measurement signals (e.g., as indicated by dashed lines 124 in FIG. 5) to be transmitted from the rotational speed sensor(s) 108 to the controller 114. As such, the controller 114 may be configured to monitor the rotational speed(s) of the rolling ground engaging component(s) based on the received measurement signals 124. For instance, the controller 114 may include a look-up table, suitable mathematical formula, and/or algorithms stored within its memory 118 that correlates the received measurement signals 124 to the rotational speed(s) of the rolling ground engaging component(s).

Thereafter, the controller 114 may be configured to determine the force(s) exerted on the rolling ground engaging component(s) by the soil. More specifically, application of the braking force(s) to the rolling ground engaging component(s) or an increase in the magnitude of the applied braking force(s) may cause the rotational speed(s) of such component(s) to decrease. Conversely, a decrease in the magnitude of the applied braking force(s) may cause the rotational speed(s) of such component(s) to increase. In this regard, the magnitude of the braking force(s) applied to the rolling ground engaging component(s) or the magnitude of the braking force adjustment(s) and the resulting change(s) in the rotational speed(s) of the rolling ground engaging component(s) may generally be indicative of the force(s) exerted on the rolling ground engaging component(s) by the soil. As such, the controller 114 may be configured to determine the force(s) exerted on the rolling ground engaging component(s) by the soil based on the magnitude of the braking force(s) applied to the rolling ground engaging component(s) or the magnitude of the braking force adjustment(s) and the resulting change(s) in the rotational speed(s). For instance, the controller 114 may include a look-up table, suitable mathematical formula, and/or algorithms stored within its memory 118 that correlates the magnitude of the braking force(s) and the change(s) in the rotational speed(s) to the force(s) exerted on the rolling ground engaging component(s) by the soil.

In several embodiments, the controller 114 may be configured to determine or estimate one or more soil characteristics for the soil within the field based on the determined force(s) exerted on the rolling ground engaging component(s). More specifically, the force(s) exerted on the rolling ground engaging component(s) by the soil may generally be indicative of various soil characteristics of the soil within the field across which the implement 10 is being moved. In this regard, the controller 114 may be configured to determine one or more soil characteristics of the soil within the field, such as the soil density, the soil plasticity, soil moisture, soil texture, the soil cohesion, and/or other inferential characteristics of the soil, based on the force(s) exerted on the rolling ground engaging component(s) by the soil. For instance, the controller 114 may include a look-up table, suitable mathematical formula, and/or algorithms stored within its memory 118 that correlates the force(s) exerted on the rolling ground engaging component(s) by the soil to the soil characteristic(s).

Furthermore, the controller 114 may be configured to monitor the determined force(s) and initiate one or more control actions when the force(s) exerted on the rolling ground engaging component(s) falls outside of an associated force range(s). Specifically, in several embodiments, the controller 114 may be configured to compare the values associated with the determined force(s) to a predetermined force range(s). Thereafter, in the event that the values of the monitored force(s) exceeds a maximum force value threshold for the given force range or falls below a minimum force value threshold for such range (thereby indicating that the force(s) exerted on the rolling ground engaging component(s) may be too high or too low), the controller 114 may be configured to initiate one or more control actions.

In one embodiment, the controller 114 may be configured to notify the operator of implement 10 that the value(s) of the monitored force(s) has fallen outside of the predetermined force range(s). Specifically, in one embodiment, the controller 114 may be communicatively coupled to the user interface 120 via a wired or wireless connection to allow feedback signals (e.g., indicated by dashed line 126 in FIG. 3) to be transmitted from the controller 114 to the user interface 120. In such embodiment, the feedback signals 126 may instruct the user interface 120 to provide a notification to the operator of the implement 10 (e.g., by causing a visual or audible notification or indicator to be presented to the operator) that provides an indication that the value of the monitored force(s) has fallen outside of the predetermined force range(s). In such instances, the operator may then choose to initiate any suitable corrective action he/she believes is necessary, such as adjusting the downforce applied to and/or the penetration depth(s) of the associated rolling ground engaging component(s).

Moreover, in several embodiments, the controller 114 may be configured to automatically adjust one or more operating parameters of the implement 10 when it is determined that the value(s) of the determined force(s) has fallen outside the predetermined force value range(s). Specifically, as shown in FIG. 5, the controller 114 may be communicatively coupled to the actuator(s) 102 of the implement 10 via a wired or wireless connection to allow control signals 122 to be transmitted from the controller 114 to the actuator(s) 102. As such, the controller 114 may be configured to transmit control signals 122 to the actuator(s) 102 instructing the actuator(s) 102 to adjust the downforce being applied to and/or penetration depth(s) of the associated rolling ground engaging component(s), such as by extending or retracting the corresponding rod(s) 104 relative to the corresponding cylinder(s) 106. Additionally, the controller 114 may be configured to automatically adjust one or more operating parameters of an associated work vehicle (e.g., via ISOBUS Class 3 communications protocols (ISO 11783-9)) when it is determined that the value(s) of the determined force(s) has fallen outside the predetermined force value range(s). For example, such operating parameter(s) of the work vehicle may include its ground speed, one or more parameters of its electro-hydraulic remotes (EHRs), and/or any other suitable parameter of the work vehicle.

Figure 6:
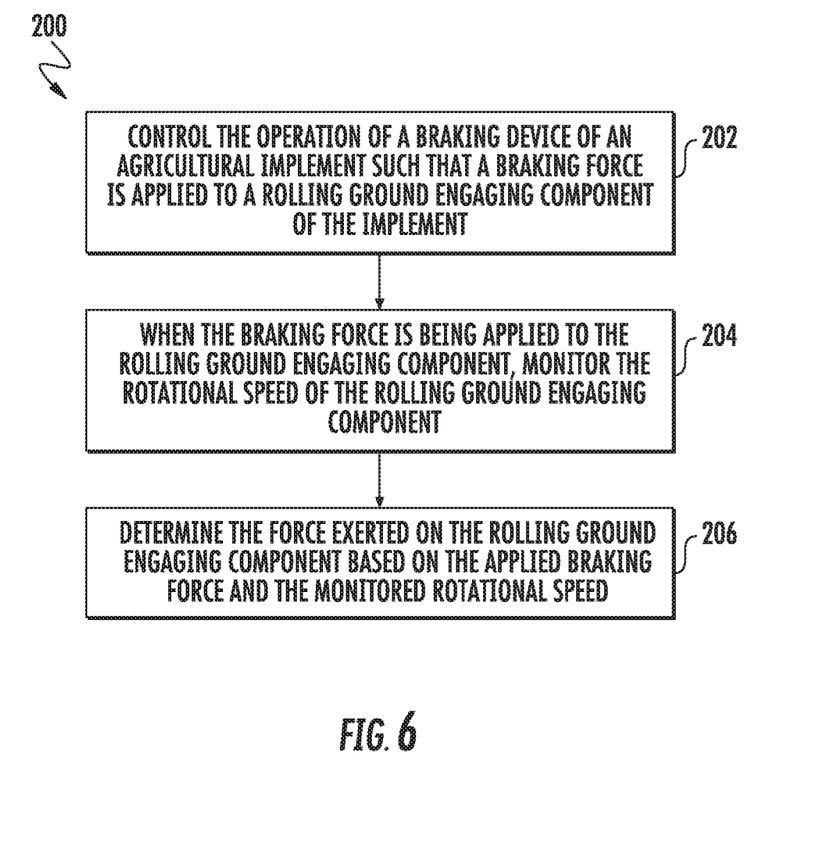
FIG. 6 is a flow diagram of one embodiment of a method for determining forces exerted on rolling ground engaging components of an agricultural implement in accordance with aspects of the present subject matter.

Referring now to FIG. 6, a flow diagram of one embodiment of a method 200 for determining forces exerted on rolling ground engaging components of an agricultural implement is illustrated in accordance with aspects of the present subject matter. In general, the method 200 will be described herein with reference to the agricultural implement 10 and the system 100 described above with reference to FIGS. 1-5. However, it should be appreciated by those of ordinary skill in the art that the disclosed method 200 may generally be utilized to determine forces exerted on rolling ground engaging components of any implement having any suitable implement configuration and/or in connection with any system having any suitable system configuration. In addition, although FIG. 6 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 6, at (202), the method 200 may include controlling, with the computing device, the operation of a braking device of an agricultural implement such that a braking force is applied to a rolling ground engaging component of the implement. For instance, as described above, the controller 114 may be configured to transmit control signals 122 to one or more braking devices 110 instructing such braking device(s) 110 to activate such that a braking force(s) is applied to a corresponding rolling ground engaging component(s), such as the gauge wheel 30, the disc opener(s) 34, the closing disc(s) 38, the press wheel 46, and/or the residue removal wheel(s) 52.

Additionally, at (204), the method 200 may include, when the braking force is being applied to the rolling ground engaging component, monitoring, with the computing device, the rotational speed of the rolling ground engaging component. For instance, as described above, the controller 114 may be communicatively coupled to one or more rotational speed sensors 108 provided in operative association with the rolling ground engaging component(s). As such, when the braking force(s) is being applied to the rolling ground engaging component(s), the controller 114 may be configured to monitor the rotational speed(s) of the rolling ground engaging component(s) based on measurement signals 124 received from the rotational speed sensor(s) 108.

Moreover, as shown in FIG. 6, at (206), the method 200 may include determining, with the computing device, the force exerted on the rolling ground engaging component based on the applied braking force and the monitored rotational speed. For instance, as described above, the controller 114 may be configured to determine or estimate the force(s) exerted on the rolling ground engaging component(s) based on the applied braking force(s), such as a magnitude(s) of the braking force(s), and the monitored rotational speed(s) of the rolling ground engaging component(s).

Figure 7:
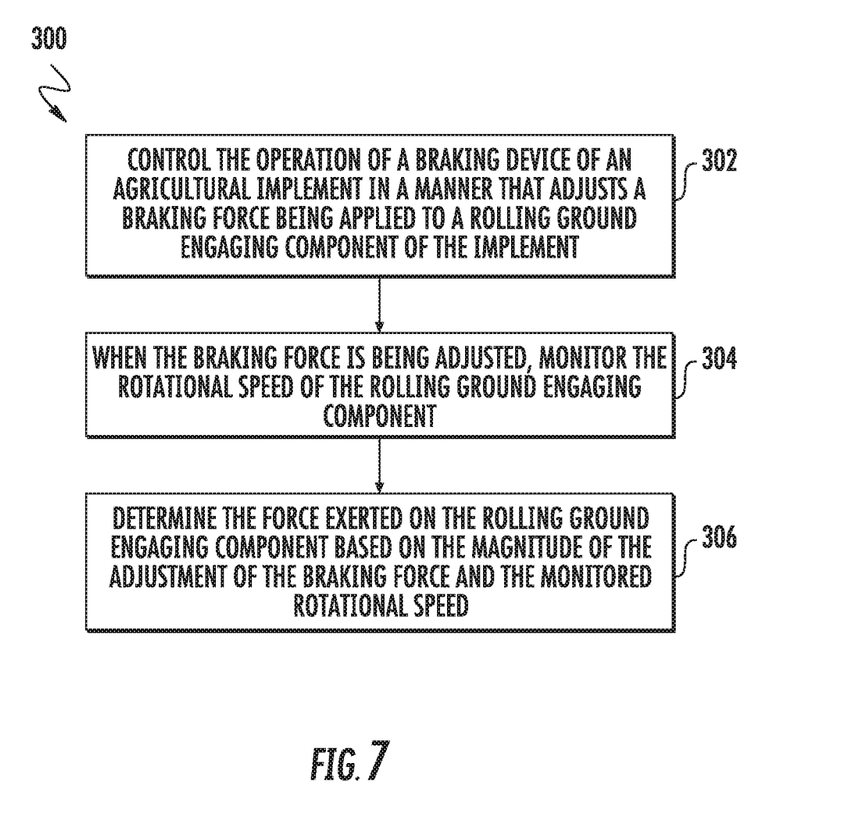
FIG. 7 is a flow diagram of another embodiment of a method for determining forces exerted on rolling ground engaging components of an agricultural implement in accordance with aspects of the present subject matter.

Referring now to FIG. 7, a flow diagram of another embodiment of a method 300 for determining forces exerted on rolling ground engaging components of an agricultural implement is illustrated in accordance with aspects of the present subject matter. In general, the method 300 will be described herein with reference to the agricultural implement 10 and the system 100 described above with reference to FIGS. 1-5. However, it should be appreciated by those of ordinary skill in the art that the disclosed method 300 may generally be utilized to determine forces exerted on rolling ground engaging components of any implement having any suitable implement configuration and/or in connection with any system having any suitable system configuration. In addition, although FIG. 7 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 7, at (302), the method 200 may include controlling, with the computing device, the operation of a braking device of an agricultural implement in a manner that adjusts a braking force being applied to a rolling ground engaging component of the implement. For instance, as described above, the controller 114 may be configured to transmit control signals 122 to one or more braking devices 110 instructing such braking device(s) 110 to adjust a braking force(s) is applied to a corresponding rolling ground engaging component(s), such as the gauge wheel 30, the disc opener(s) 34, the closing disc(s) 38, the press wheel 46, and/or the residue removal wheel(s) 52.

Additionally, at (304), the method 200 may include, when the braking force is being adjusted, monitoring, with the computing device, the rotational speed of the rolling ground engaging component. For instance, as described above, the controller 114 may be communicatively coupled to one or more rotational speed sensors 108 provided in operative association with the rolling ground engaging component(s). As such, when the braking force(s) is being adjusted, the controller 114 may be configured to monitor the rotational speed(s) of the rolling ground engaging component(s) based on measurement signals 124 received from the rotational speed sensor(s) 108.

Moreover, as shown in FIG. 7, at (306), the method 200 may include determining, with the computing device, the force exerted on the rolling ground engaging component based on the magnitude of the adjustment of the braking force and the monitored rotational speed. For instance, as described above, the controller 114 may be configured to determine or estimate the force(s) exerted on the rolling ground engaging component(s) based on the magnitude of the adjustment of the braking force(s) and the monitored rotational speed(s) of the rolling ground engaging component(s).

It is to be understood that the steps of the methods 200 and 300 are performed by the controller 114 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 114 described herein, such as the methods 200 and 300, is implemented in software code or instructions which are tangibly stored on a tangible computer readable medium. The controller 114 loads the software code or instructions via a direct interface with the computer readable medium or via a wired and/or wireless network. Upon loading and executing such software code or instructions by the controller 114, the controller 114 may perform any of the functionality of the controller 114 described herein, including any steps of the methods 200 and 300 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

The invention claimed is:

1. A system for determining forces exerted on rolling ground engaging components of an agricultural implement, the system comprising:
   a rolling ground engaging component configured to roll relative to soil within a field as the agricultural implement is moved across the field;
   a braking device configured to apply a braking force to the rolling ground engaging component;
   a sensor configured to detect a parameter indicative of a rotational speed of the rolling ground engaging component; and
   a controller communicatively coupled to the sensor, the controller configured to:
      control an operation of the braking device such that a braking force is applied to the rolling ground engaging component;
      when the braking force is being applied to the rolling ground engaging component, monitor the rotational speed of the rolling ground engaging component based on measurement signals received from the sensor; and
      determine a force exerted on the rolling ground engaging component by the soil within the field based on the applied braking force and the monitored rotational speed.

2. The system of claim 1, wherein the controller is further configured to determine a soil characteristic for the soil within the field based on the determined force.

3. The system of claim 2, wherein the soil characteristic comprises at least one of a soil density of the soil, a soil plasticity of the soil, a soil moisture of the soil, a soil texture of the soil, or a soil cohesion of the soil.

4. The system of claim 1, wherein the controller is further configured to monitor the determined force relative to a predetermined force range and initiate a control action when the monitored force exceeds a predetermined maximum force threshold of the predetermined force range or falls below a predetermined minimum force threshold of the predetermined force range.

5. The system of claim 4, wherein the control action comprises notifying an operator of the agricultural implement that the monitored force has fallen outside of the predetermined force range.

6. The system of claim 4, wherein the control action comprises adjusting an operating parameter of the agricultural implement.

7. The system of claim 6, wherein the operating parameter comprises a downforce applied to the rolling ground engaging component.

8. The system of claim 1, wherein the braking device comprises a non-contact-based braking device.

9. The system of claim 1, further comprising:
   a clutch configured to selectively transmit the braking force from the braking device to the rolling ground engaging component.

10. The system of claim 1, wherein the rolling ground engaging component comprises at least one of a closing disc, a gauge wheel, a disc opener, a packer wheel, or a residue removal device.

11. A system for determining forces exerted on rolling ground engaging components of an agricultural implement, the system comprising:
   a rolling ground engaging component configured to roll relative to soil within a field as the agricultural implement is moved across the field;
   a braking device configured to apply a braking force to the rolling ground engaging component;
   a sensor configured to detect a parameter indicative of a rotational speed of the rolling ground engaging component; and
   a controller communicatively coupled to the sensor, the controller configured to:
      control an operation of the braking device in a manner that adjusts a braking force being applied to the rolling ground engaging component;
      when the braking force is being adjusted, monitor the rotational speed of the rolling ground engaging component based on measurement signals received from the sensor; and
   determine a force exerted on the rolling ground engaging component by the soil within the field based on a magnitude of an adjustment of the braking force and the monitored rotational speed.

12. The system of claim 11, wherein adjusting the braking force comprises decreasing the braking force.

13. A method for determining forces exerted on rolling ground engaging components of an agricultural implement, the agricultural implement including a rolling ground engaging component configured to roll relative to soil within a field as the agricultural implement is moved across the field, the method comprising:

controlling, with the computing device, an operation of a braking device such that a braking force is applied to the rolling ground engaging component;

when the braking force is being applied to the rolling ground engaging component, monitoring, with the computing device, a rotational speed of the rolling ground engaging component; and determining, with the computing device, a force exerted on the rolling ground engaging component based on the applied braking force and the monitored rotational speed.

14. The method of claim 13, further comprising:
determining, with the computing device, a soil characteristic for the soil within the field based on the determined force.

15. The method of claim 14, wherein the soil characteristic comprises at least one of a soil density of the soil, a soil plasticity of the soil, a soil moisture of the soil, a soil texture of the soil, or a soil cohesion of the soil.

16. The method of claim 13, further comprising:
monitoring, with the computing device, the force relative to a predetermined force range and initiate a control action when the monitored force exceeds a predetermined maximum force threshold of the predetermined force range or falls below a predetermined minimum force threshold of the predetermined force range.

17. The method of claim 16, wherein the control action comprises notifying an operator of the agricultural implement that the monitored force has fallen outside of the predetermined force range.

18. The method of claim 16, wherein the control action comprises adjusting an operating parameter of the agricultural implement.

19. The method of claim 18, wherein the operating parameter comprises a downforce applied to the rolling ground engaging component.

20. The method of claim 13, further comprising:
controlling, with the computing device, an operation of a clutch such that the braking force is transmitted from the braking device to the rolling ground engaging component.

* * * * *